United States Patent [19]

Hocquaux et al.

[11] Patent Number: 5,328,914
[45] Date of Patent: Jul. 12, 1994

[54] USE OF PYRIMIDINE 3-OXIDE DERIVATIVES FOR SLOWING DOWN HAIR LOSS AND TOPICAL COMPOSITIONS USED

[75] Inventors: Michel Hocquaux, Paris; Jacqueline Dumats, Villepinte; Jean B. Galey, Paris, all of France

[73] Assignee: L'Oreal, Paris, France

[21] Appl. No.: 956,507
[22] PCT Filed: Jul. 19, 1991
[86] PCT No.: PCT/FR91/00596
  § 371 Date: Jan. 19, 1993
  § 102(e) Date: Jan. 19, 1993
[87] PCT Pub. No.: WO92/01437
  PCT Pub. Date: Feb. 6, 1992

[30] Foreign Application Priority Data

Jul. 20, 1990 [LU] Luxembourg .......................... 87766

[51] Int. Cl.⁵ .................. A61K 7/06; A61K 31/505; A01N 43/54
[52] U.S. Cl. ................................ 514/310; 514/256; 514/272; 514/320; 424/70
[58] Field of Search ............... 514/310, 256, 272, 320; 424/70; 252/182.12, 182.15, 182.16

[56] References Cited

U.S. PATENT DOCUMENTS 4,973,474  11/1990  Hocquaux et al. .................. 424/70

FOREIGN PATENT DOCUMENTS

| 0064012 | 11/1982 | European Pat. Off. . |
| 0211610 | 2/1987 | European Pat. Off. . |
| 0277428 | 8/1988 | European Pat. Off. . |
| 0334586 | 9/1989 | European Pat. Off. . |
| 0375388 | 6/1990 | European Pat. Off. . |
| 0403238 | 12/1990 | European Pat. Off. . |
| 1477048 | 4/1967 | France . |
| 2091516 | 1/1972 | France . |
| 2169787 | 9/1973 | France . |
| 2328763 | 5/1977 | France . |
| 2574786 | 6/1986 | France . |
| 2581542 | 11/1986 | France . |

WO89/07595  8/1989  World Int. Prop. O. .
WO92/01437  2/1992  World Int. Prop. O. .

OTHER PUBLICATIONS

Interscience Pub., Supplement II, vol. 16, Chapter X, p. 360, 1985.
Aust. J. Chem., 34, 1539, 1981.

*Primary Examiner*—Arthur C. Prescott
*Attorney, Agent, or Firm*—Jacobson, Price, Holman & Stern

[57] ABSTRACT

Pyrimidine 3-oxide derivatives and their use for the treatment of hair loss. The compositions contain in a physiologically acceptable medium at least one compound corresponding to the formula (I):

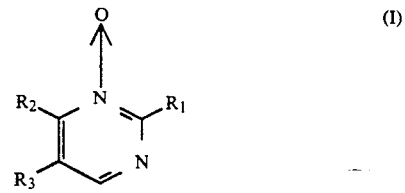

in which:

$R_1$ denotes a methyl or $NHR_4$ group in which $R_4$ denotes a $C_1$-$C_4$ alkyl group or hydrogen;

$R_2$ denotes hydrogen or a group $NHR_4$ in which $R_4$ has the same meaning as above; $R_2$ may also denote methyl when $R_1$ denotes methyl; when $R_1$ denotes $NH_2$, $R_2$ cannot be hydrogen;

$R_3$ may denote a hydrogen atom or a $C_1$-$C_4$ alkyl group which may optionally carry;

a group $OR_5$ in which $R_5$ denotes a $C_1$-$C_4$ alkyl group, a benzene nucleus which is optionally substituted by one or more $C_1$-$C_4$ alkoxy groups;

$R_3$ may also denote a halogen atom or a nitro or amino group;

and the physiologically acceptable acid addition salts.

19 Claims, No Drawings

USE OF PYRIMIDINE 3-OXIDE DERIVATIVES FOR SLOWING DOWN HAIR LOSS AND TOPICAL COMPOSITIONS USED

The present invention relates to the use of pyrimidine 3-oxide derivatives for slowing down hair loss and to the compositions containing these derivatives and intended for topical application to the scalp.

Compounds which are effective for the treatment of hair loss without, however, exhibiting side effects which could be inconvenient during prolonged application have been sought for many years.

Mucopolysaccharide-based compositions which are used for slowing down hair loss are particularly known.

The applicant company has discovered new pyrimidine 3-oxide derivatives which are particularly effective for slowing down hair loss. In particular, it has observed an increase in the number of hairs in the anagen phase or in the growth phase and a decrease in the number of hairs in the telogen phase or in the terminal phase of the hair. The increase in the ratio of the number of hairs in the anagen phase to the number of hairs in the telogen phase is an indication of the effect of these compounds on the treatment of hair loss. Moreover, these compounds have the advantage of not having side effects which may be inconvenient during prolonged application.

The subject of the invention is the use of pyrimidine 3-oxide derivatives for slowing down hair loss.

Another subject of the invention consists of the topical compositions intended for use in slowing down hair loss.

Other subjects of the invention will become apparent on reading the following description and examples.

The compounds used in conformity with the invention for slowing down hair loss are of the general formula:

$$\text{(I)}$$

in which:
  $R_1$ denotes a methyl or $NHR_4$ group in which $R_4$ denotes a $C_1$–$C_4$ alkyl group or a hydrogen atom;
  $R_2$ denotes hydrogen or a group $NHR_4$ in which $R_4$ has the same meaning as above; $R_2$ may also denote methyl when $R_1$ denotes methyl; when $R_1$ denotes $NH_2$, $R_2$ cannot be hydrogen;
  $R_3$ may denote a hydrogen atom a $C_1$–$C_4$ alkyl group which may optionally carry:
    a group $OR_5$ in which $R_5$ denotes a $C_1$–$C_4$ alkyl group,
    a benzene nucleus which is optionally substituted by one or more $C_1$–$C_4$ alkoxy groups;
  $R_3$ may also denote a halogen atom or a nitro or amino group;
  and the physiologically acceptable acid addition salts.

An alkyl group preferably denotes, in conformity with the invention, a methyl or ethyl group, the alkoxy group preferably denotes methoxy or ethoxy, the halogen atoms preferably denote chlorine or bromine.

The preferred compounds which may be used in conformity with the invention are the compounds corresponding to the formula (I) in which $R_1$ denotes amino, $R_2$ denotes amino and $R_3$ denotes hydrogen or alternatively $R_1$ denotes amino, $R_2$ denotes amino and $R_3$ denotes chlorine.

The compounds corresponding to the general formula (I) can also be obtained for example by hydrogenolysis, in the presence of palladium on charcoal, of compounds corresponding to the formula (II) which is defined below, in which Z denotes a halogen atom and preferably chlorine or bromine.

The reduction is performed according to the conventional method described in the literature (D. J. Brown, The pyrimidines, supplement II, Vol. 16, chapter X, page 360, Interscience Pub. 1985; Cowden and Waring, Aust. J. Chem. 94, 1539 (1981) according to the following reaction scheme:

$$\text{(II)} \xrightarrow{\text{Pd/C, } H_2} \text{(I)}$$

The compounds of formula (I) can also be used in the form of their physiologically acceptable acid additional salts such as the salts of sulfuric, hydrochloric, phosphoric, acetic, benzoic, salicylic, glycolic, aceturic, succinic, nicotinic, tartaric, maleic, pamoic [sic], methanesulfonic, picric and lactic acid, of amino acids and more particularly of aceturic acid.

These compounds are generally used for the treatment of hair loss in compositions which can be provided in the form of a lotion, shampoo, gel, foam, emulsion, vesicular dispersion, soap, spray or aerosol foam.

The compositions intended for topical application are essentially characterized in that they contain, in a physiologically acceptable medium appropriate for topical application, at least one compound Corresponding to the formula (I) or one of its acid addition salts defined above.

The compound of formula (I) is present in proportions of between 0.1 and 10% by weight and preferably between 0.2 and 5% by weight relative to the total weight of the composition.

The physiologically acceptable medium may consist of any medium appropriate for a topical application, either in the cosmetic field or in the pharmaceutical field, which is compatible with the active substance. The compounds conforming to the invention may be present in this medium either in the dissolved state or in the dispersed state, especially in micronized form.

The physiologically acceptable medium may consist of water or a mixture of water and a solvent or a mixture of solvents. The solvents are chosen from cosmetically or pharmaceutically acceptable organic solvents and are chosen more particularly from $C_1$–$C_4$ lower alcohols such as ethyl alcohol, isopropyl alcohol, tertbutyl alcohol, alkylene glycols, alkylene glycol and dialkylene glycol alkyl ethers such as ethylene glycol monoethyl ether, propylene glycol monomethyl ether and diethylene glycol monoethyl ether. The solvents, when they are present, are in proportions of between 1 and 80% by weight relative to the total weight of the composition.

The medium may be thickened by means of thickening agents commonly used in the cosmetic or pharmaceutical field.

The thickeners are preferably present in proportions of between 0.1 and 5% by weight and in particular between 0.4 and 3% by weight relative to the total weight of the composition.

These compositions may also contain:
esterified oligosaccharides such as those described in EP-A-0,211,610 and EP-A-0,064,012;
hexosaccharic acid derivatives such as those described in EP-A-0,375,388, in particular glucosaccharic acid;
glycosidase inhibitors such as those described in EP-A-0,334,586, in particular D-glucaro-1,5-lactam;
glycosaminoglycanase and proteoglycanase inhibitors such as those mentioned in EP-A-0,277,428, in particular L-galactono-1,4-lactone;
tyrosine kinase inhibitors such as those described in EP-A-0,403,238, in particular 1-amido1-cyano-(3,4-dihydroxyphenyl)ethylene;
hyperemics such as:
  nicotinic acid esters including more particularly benzyl and $C_1$–$C_6$ alkyl nicotinates, and especially methyl and benzyl nicotinate, as well as tocopherol nicotinate;
  xanthine bases including more particularly caffeine and theophylline;
  capsicin;
UV-A- and UV-B-screening agents such as methoxycinnamates and benzophenone derivatives;
phosphodiesterase inhibitors such as Visnadine ®;
adenine cyclase activators such as Forskolin;
antioxidants and free radical scavengers, in particular OH radicals such as DMSO;
  α-tocopherol, BHA, BHT;
  superoxide dismutase (SOD);
antidandruff agents such as omadine and octopirox;
moisturizing agents such as urea, glycerine, lactic acid, α-hydroxyacids, thiamorpholinone and its derivatives, and lactones;
antiseborrheic agents such as S-carboxymethylcysteine, S-benzylcysteamine and their derivatives, and thioxolone;
steroidal and nonsteroidal anti-inflammatory agents such as hydrocortisone, betamethasone, dexamethasone and niflumic acid;
antiandrogens and hormones such as estriol, estradiol, thyroxine, oxendolone and diethylstilbestrol;
retinoids including more particularly alltrans-retinoic acid also called tretinoin, isotretinoin, retinol or vitamin A and its derivatives such as the acetate, palmirate or propionate, motretinide, etretinate, and zinc all-trans-retinoate;
antibacterials chosen more particularly from macrolides, pyranosides and tetracyclines, and especially erythromycin;
calcium antagonists among which Cinnarizine and Diltiazem may be mentioned by way of nonlimiting examples;
phospholipids such as lecithin;
diazoxide (3-methyl-7-chloro[2H]-1,2,4-benzothiadiazine 1,1-dioxide);
linoleic and linolenic acids;
anthralin and its derivatives;
5-alkanoylsalicylic acid and its derivatives as described in Patent FR-25 81 542;
penetration activators such as THF, 1,4-dioxane, oleyl alcohol, 2-pyrrolidone, benzyl salicylate and the like;
vitamins or provitamins such as β-carotene, biotin, panthenol and its derivatives, vitamin C, and vitamins $B_2$, $B_4$ and $B_6$.

These compositions may also contain cyclic AMP and MPS.

These compositions may also contain preservatives, stabilizers, pH-regulating agents, osmotic pressure modifying agents and emulsifiers.

The compounds conforming to the invention may also be combined with surface-active agents including especially those chosen from nonionic and amphoteric surface-active agents.

Among the nonionic surface-active agents, there may be mentioned the polyhydroxypropyl ethers described especially in French Patents Nos. 1,477,048; 2,091,516; 2,169,787; 2,328,763 and 2,574,786; oxyethylenated ($C_8$–$C_9$)alkylphenols containing from 1 to 100 moles of ethylene oxide and preferably 5 to 35 moles of ethylene oxide; and alkylpolyglycosides of formula:

$$C_nH_{2n+1}(C_6H_{10}O_5)_xH \qquad (III)$$

in which n ranges from 8 to 15 inclusive and x from 1 to 10 inclusive.

Among the amphoteric surface-active agents, there may be mentioned more particularly the amphocarboxyglycinates and the amphocarboxypropionates defined in the CTFA dictionary, 3rd edition, 1982, and sold especially under the name Miranol ® by the company Miranol.

The compounds according to the invention may be introduced into carriers which further improve the regrowth activity while at the same time possessing advantageous properties from the cosmetic point of view, such as ternary volatile mixtures of alkylene glycol alkyl ethers, especially $C_1$–$C_4$ alkyl, $C_1$–$C_4$ alkylene glycol or dialkylene glycol, preferably $C_1$–$C_4$ dialkylene glycol, of ethyl alcohol and of water; the preferred alkylene glycol alkyl ethers are ethylene glycol monoethyl ethers, propylene glycol monomethyl ether and diethylene glycol monomethyl ether.

Cationic and/or anionic surface-active agents may also be used.

The compounds conforming to the invention may also be introduced into gelled or thickened carriers such as essentially aqueous carriers gelled by means of heterobiopolysaccharides, such as xanthan gum, scleroglucans or cellulose derivatives, in particular cellulose ethers, aqueous alcoholic carriers gelled by means of polyhydroxyethyl acrylates or methacrylates or essentially aqueous carriers thickened in particular by means of polyacrylic acids crosslinked by means of a polyfunctional agent such as the Carbopols sold by the company Goodrich.

The subject of the invention is also a process for the cosmetic treatment of hair or of the scalp, consisting in applying to them at least one composition as defined above, for the purpose of improving the appearance of the hair.

The treatment mainly consists in applying the composition as defined above to the alopecic areas of the scalp of an individual.

The preferred method of application consists in applying 1 to 2 g of the composition to the alopecic area, at a rate of one to two applications per day, for 1 to 7 days per week and this for a period of 1 to 6 months.

The subject of the invention is also a composition intended for the therapeutic treatment of hair loss, especially alopecia, this composition corresponding to the definition of the compositions for topical application defined above.

The following examples are intended to illustrate the invention without, however, being of a limiting nature.

EXAMPLES OF COMPOSITION

EXAMPLE 1

The following composition is prepared:

| | |
|---|---|
| 2,4-diaminopyrimidine 3-oxide | 3 g |
| propylene glycol | 20 g |
| 95° ethanol | 30 g |
| water q.s. | 100 g |

This composition is provided in the form of a lotion.

EXAMPLE 2

The following composition is prepared:

| | |
|---|---|
| 2,4-diaminopyrimidine 3-oxide | 1.05 g |
| methyl nicotinate | 0.105 g |
| perfume | 0.26 g |
| absolute ethanol | 29.5 g |
| water q.s. | 100 g |

This composition is provided in the form of a lotion.

1 to 2 g of the compositions described in Examples 1 and 2 are applied to the alopecic areas of the scalp, the application being optionally accompanied by a massage to enhance penetration, at a rate of one to two applications per day, for three months of treatment.

A reduction in hair loss is observed.

EXAMPLE 3

The following composition is prepared:

| | |
|---|---|
| 2,4-diaminopyrimidine 3-oxide | 1.05 g |
| perfume | 0.26 g |
| absolute ethanol | 29.5 g |
| water q.s. | 100 g |

This composition is provided in the form of a lotion.

EXAMPLE 4

The following lotions (A) and (B) are prepared:

| | |
|---|---|
| LOTION (A) | |
| 2,4-diamino-5-chloropyrimidine 3-oxide | 1.5 g |
| propylene glycol | 20 g |
| ethanol | 30 g |
| purified water q.s. | 100 g |
| LOTION (B) | |
| Visnadine | 3 g |
| propylene glycol | 5 g |
| absolute ethanol q.s. | 100 g |

Lotion (A) is applied in the morning to the alopecic areas of the scalp while massaging if desired, followed by the application of lotion (B) in the evening. A decrease in hair loss is observed after a few months of treatment.

EXAMPLE 5

The following lotions (A) and (B) are prepared:

| | |
|---|---|
| LOTION (A) | |
| 5-octanoylsalicylic acid | 0.5 g |
| ethanol | 50 g |
| purified water q.s. | 100 g |
| LOTION (B) | |
| 2,4-diaminopyrimidine 3-oxide | 2 g |
| propylene glycol | 20 g |
| ethanol | 50 g |
| purified water q.s. | 100 g |

Lotion (A) is applied in the morning to the alopecic areas of the scalp while massaging if desired, followed by the application of lotion (B) in the evening. A decrease in hair loss is observed after a few months of treatment.

EXAMPLE 6

The following solutions (A) and (B) are prepared:

| | |
|---|---|
| SOLUTION (A) | |
| 2,4-diaminopyrimidine 3-oxide | 2.5 g |
| propylene glycol | 7 g |
| absolute ethanol q.s. | 100 g |
| SOLUTION (B) | |
| retinoic acid (all-trans) | 0.05 g |
| propylene glycol | 7 g |
| absolute ethanol q.s. | 100 g |

Solutions (A) and (B) are stored in a two-compartment kit.

A 50/50 mixture of components (A) and (B) gives 1.25% of 2,4-diaminopyrimidine 3-oxide+0.025% of retinoic acid to.

This mixture is applied to the alopecic areas of the scalp, without rinsing the composition after application.

EXAMPLE 7

The following lotion is prepared:

| | |
|---|---|
| 2,4-diaminopyrimidine 3-oxide | 2.5 g |
| Diltiazem | 1 g |
| propylene glycol | 20 g |
| ethanol | 55 g |
| purified water q.s. | 100 g |

This lotion is applied to the alopecic areas of the scalp without subsequent rinsing.

EXAMPLE 8

The following lotion is prepared:

| | |
|---|---|
| 2,4-diaminopyrimidine 3-oxide | 2 g |
| hydrocortisone | 0.5 g |
| propylene glycol | 7 g |
| absolute ethanol q.s. | 100 g |

This lotion is applied to the alopecic areas of the scalp without subsesquent rinsing.

EXAMPLE 9

The following composition is prepared:

| ANTHRALIN-CONTAINING GEL | |
|---|---|
| anthralin | 0.1 g |
| silica sold under the name Silica HDK N 20 by the company Wacker Chemie | 3 g |
| butyl stearate q.s. | 100 g |

This composition is applied to the alopecic areas of the scalp. The product is allowed to act for half an hour. A shampoo of the following composition is applied:

| | |
|---|---|
| 2.4-diaminopyrimidine 3-oxide | 1 g |
| nonionic surfactant prepared by condensation of 3.5 moles of glycidol with a $C_{11}$ to $C_{14}$ α-diol according to FR-A-2,091,516 | 26 g AS |
| hydroxypropylcellulose sold under the name Klucel G by the company Hercules | 2 g |
| preservatives q.s. | |
| ethanol | 50 g |
| purified water q.s. | 100 g |

The scalp thus treated is rinsed.

EXAMPLE 10

The following lotion is prepared:

| | |
|---|---|
| 2,4-diaminopyrimidine 3-oxide | 1.5 g |
| biotin ethyl ester | 1 g |
| propylene glycol | 20 g |
| ethanol q.s. | 100 g |

This composition is applied to the alopecic areas of the scalp without subsequent rinsing.

EXAMPLE 11

The following niosome-containing gel is prepared:

| | |
|---|---|
| 2,4-diaminopyrimidine 3-oxide | 0.5 g |
| eucalyptus essential oil | 1 g |
| nonionic surfactant of formula: with R = $C_{12}H_{22}$ R' = $C_{14}H_{29}/C_{16}H_{33}$ according to FR-2,465,780. | 1.9 g |
| Na-glutamate of hydrogenated tallow, sold under the name Acylglutamate HS 110 by the company Ajinomoto | 0.1 g |
| Carbopol 934 P sold by the company B.F. Goodrich Corporation | 0.3 g AS |
| preservatives q.s. | |
| neutralizing agent q.s.  pH = 7 | |
| purified water q.s. | 100 g |

EXAMPLE 12

The following lotion is prepared:

| | |
|---|---|
| 2,4-diaminopyridine 3-oxide | 1.5 g |
| Octopirox | 0.2 g |
| ethanol | 45 g |
| purified water q.s. | 100 g |

This composition is applied to the alopecic areas of the scalp without subsequent rinsing.

EXAMPLE 13

The following composition is prepared:

| | |
|---|---|
| 2,4-diaminopyrimidine 3-oxide | 1 g |
| sunscreen agent sold under the name Uvinul MS 40 by the company BASF | 1 g |
| vitamin F | 0.1 g |
| BHA | 0.025 g |
| BHT | 0.025 g |
| nonionic surface-active agent sold under the name Polawax A 31 Croda by the company Croda | 0.5 g |
| ethanol | 50 g |
| purified water q.s. | 100 g |

This composition is introduced into a container under pressure, in an amount of 95% of composition per 5% of hydrocarbon propellant.

At the outlet from the container, a foam is formed which is applied to the alopecic areas of the scalp.

EXAMPLE OF PREPARATION 1

2,4-Diaminopyrimidine 3-oxide (I)

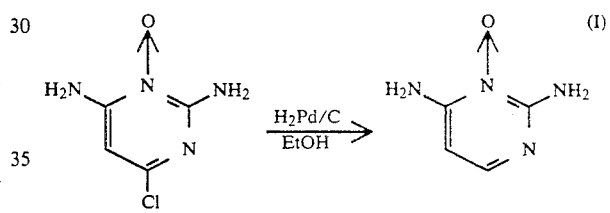

This derivative is prepared by hydrogenolysis of 2,4-diamino-6-chloropyrimidine 3-oxide.

Procedure 15 g of 2,4-diamino-6-chloropyrimidine 3-oxide are dissolved in a solution containing 5.9 g of potassium hydroxide in 1000 cm³ of absolute ethanol.

After 2.3 g of 10% palladium on charcoal have been added, the mixture is stirred under a hydrogen atmosphere for 2 hours.

The catalyst is filtered, washed with ethanol and the organic phase is evaporated.

The residue obtained is recrystallized from water.

9 g of white precipitate are obtained (67% yield). M.p.=192° C.

Elemental analysis:

$C_4H_6N_4O$  $H_2O$;  MW=144.

| | C | H | N | O |
|---|---|---|---|---|
| Calculated | 33.33 | 5.56 | 38.89 | 22.22 |
| Found | 33.46 | 5.60 | 39.02 | 22.50 |

The ¹H NMR and mass spectra are consistent with the expected structure.

EXAMPLE OF PREPARATION 2

2,4-Diamino-5-chloropyrimidine 3-oxide

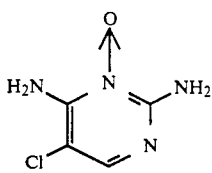

Procedure 10 g of 2,4-diaminopyrimidine 3-oxide are dissolved in 600 ml of methanol, in a 1-1 three-necked round bottom flask provided with a condenser, a thermometer and mechanical stirring.

13.9 g of N-chlorosuccinimide are added at room temperature. The mixture is stirred for 3 h at 55° C.

The reaction mixture is evaporated to dryness and then taken up in 50 ml of water. The pH is adjusted to 8 by adding concentrated sodium hydroxide.

The product is filtered, washed with 50 ml of ice cold water and recrystallized from 50 ml of water.

4.5 g of 2,4-diamino-5-chloropyrimidine 3-oxide are obtained.

Yield = 40% M.p. = 220° C.

Elemental analysis:

$C_4H_5N_4O\ Cl$

|  | C | H | N | O | Cl |
|---|---|---|---|---|---|
| Calculated | 28.93 | 3.37 | 33.75 | 12.53 | 21.40 |
| Found | 28.94 | 3.46 | 33.62 | 12.47 | 21.53 |

The $^1H$ and $^{13}C$ NMR spectra as well as the mass spectrum are consistent with the expected structure.

EXAMPLE OF PREPARATION 3

2,4-Diamino-5-ethylpyrimidine 3-oxide

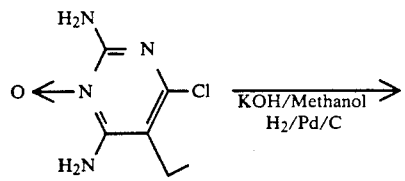

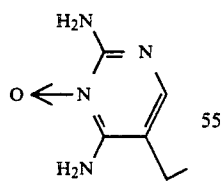

The following are placed in a hydrogenation bottle of a Parr apparatus:
- 1.15 g of potassium hydroxide dissolved in 300 ml of methanol
- 0.42 g of 10% palladium on charcoal
- 3 g of 2,4-diamino-5-ethyl-6-chloropyrimidine 3-oxide.

The bottle is charged with hydrogen to 30 psi. After stirring for 3 hours, the bottle is purged with nitrogen. The reaction mixture is filtered on paper. The filtrates are evaporated to dryness. The residue is recrystallized from water and then from an isopropanol/water mixture.

800 mg of 2,4-diamino-5-ethylpyrimidine 3-oxide are obtained. Yield = 33%.

Elemental analysis $C_6H_{10}N_4O$; $M = 154$

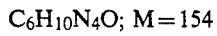

|  | C | H | N | O |
|---|---|---|---|---|
| Calculated | 46.75 | 6.49 | 36.36 | 10.39 |
| Found | 46.80 | 6.55 | 36.45 | 10.47 |

The $^1H$ NMR and mass spectra are consistent with the expected structure.

EXAMPLE OF PREPARATION 4

2-Methyl-4-amino-5-chloropyrimidine 3-oxide

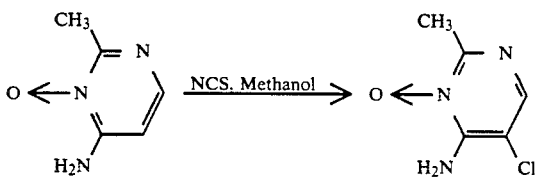

6.3 g of 2-methyl-4-aminopyrimidine 3-oxide are dissolved in 150 ml of methanol. 7.05 g of N-chlorosuccinimide are added. The reaction mixture is stirred for 24 hours at room temperature. It is evaporated to dryness. The residue is taken up in 50 ml of acetone. The precipitate is filtered and then taken up in 150 ml of water. The pH is adjusted to 8 by adding concentrated sodium hydroxide. After stirring for half an hour, the precipitate is filtered. It is recrystallized from an acetonitrile/water mixture (70/30).

1.20 g of 2-methyl-4-amino-5-chloropyrimidine 3-oxide are obtained.

Yield = 15%.

Melting point = 209° C.

Elemental analysis $C_5H_6ClN_3O$; $M = 159.5$

|  | C | H | N | O | Cl |
|---|---|---|---|---|---|
| Calculated | 37.62 | 3.76 | 26.33 | 10.03 | 22.25 |
| Found | 37.54 | 3.79 | 26.23 | 10.02 | 22.20 |

The $^1H$ NMR and mass spectra are consistent with the expected structure.

EXAMPLE OF PREPARATION 5

2,4-Diamino-5-bromopyrimidine 3-oxide

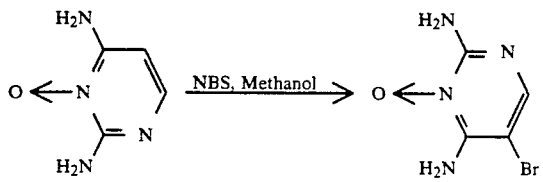

1 g of 2,4-diaminopyrimidine 3-oxide is dissolved in 60 ml of methanol. 1.55 g of N-bromosuccinimide are added. The reaction mixture is stirred for 2 hours at 60°

C. It is evaporated to dryness. The residue is taken up in 5 ml of water. The pH is adjusted to 8 by adding concentrated sodium hydroxide. After stirring for half an hour, the precipitate is filtered on sintered glass, rinsed with 5 ml of water and then with 2×25 ml of acetone. It is recrystallized from an ethanol/water mixture (50/50).

700 mg of 2,4-diamino-5-bromopyrimidine 3-oxide are obtained.

Yield =50%

Melting point: decomposition from 245° C.

Elemental analysis:

$C_4H_5BrN_4O$; M=205

|  | C | H | N | O | Br |
|---|---|---|---|---|---|
| Calculated | 23.41 | 2.44 | 27.32 | 7.80 | 39.02 |
| Found | 23.36 | 2.45 | 27.38 | 8.01 | 38.84 |

The $^1$H NMR and mass are consistent with the expected structure.

EXAMPLE OF PREPARATION 6

2-Methyl-4-aminopyrimidine 3-oxide

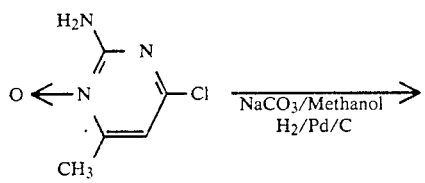

The following are placed in a hydrogenation bottle of a Parr apparatus:

3.65 g of sodium carbonate
335 ml of methanol
0.8 g of 10% palladium on carbon
5 g of 2-methyl-4-amino-6-chloropyrimidine 3-oxide.

The bottle is charged with hydrogen to 30 psi. After stirring for 3 hours, the system is purged with argon. The reaction mixture is filtered on filter paper. The filtrates are evaporated to dryness. The precipitate obtained is taken up in 50 ml of boiling acetonitrile. The insoluble matter is filtered on sintered glass and then recrystallized from 60 ml of ethanol. 1.1 g of 2-methyl-4-aminopyrimidine 3-oxide are recovered.

Yield =28%

Melting point:=246° C.

Elemental analysis:

$C_5h_7N_3O$; M=125

|  | C | H | N | O |
|---|---|---|---|---|
| Calculated | 48.00 | 5.60 | 33.60 | 12.80 |
| Found | 47.62 | 5.69 | 33.75 | 13.00 |

The $^1$H NMR and mass spectra are consistent with the expected structure.

EXAMPLE OF PREPARATION 7

Preparation of the nicotinic acid salt of 2,4-diaminopyrimidine 3-oxide

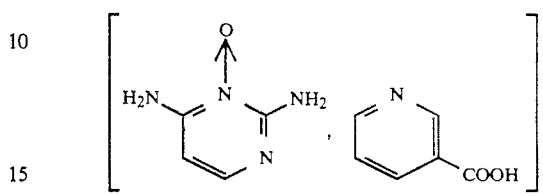

A mixture of 2 g of 2,4-diaminopyrimidine 3-oxide and 1.71 g of nicotinic ac [sic]is recrystallized from 20 ml of ethanol. A white solid is recovered which is dried to obtain 2.90 g of 2,4-diaminopyrimidine 3-oxide and nicotinic acid salt.

Yield=78%

Melting Point:=173°-176° C.

Elemental analysis:

$C_{10}H_{11}N_5O_3 + 0.36H_2O$

|  | C | H | N | O |
|---|---|---|---|---|
| Calculated | 46.93 | 4.55 | 27.34 | 21.02 |
| Found | 47.07 | 4.56 | 27.49 | 21.08 |

EXAMPLE OF PREPARATION 8

Preparation of 2,4-diaminopyrimidine 3-oxide aceturate

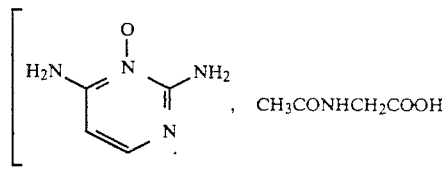

A mixture of 2 g of 2,4-diaminopyrimidine 3-oxide and 1.62 g of aceturic acid is recrystallized from 20 ml of ethanol. A white solid is recovered which is dried to obtain 3.5 g of 2,4-diainopyrimidine 3-oxide aceturate salt.

Yield=96%

Melting point:=133°-134 C.

Elemental analysis:

$C_8H_{13}N_5O_4 + 0.75H_2O$

|  | C | H | N | O |
|---|---|---|---|---|
| Calculated | 37.42 | 5.65 | 27.29 | 29.63 |
| Found | 37.42 | 5.63 | 27.45 | 29.92 |

EXAMPLE OF PREPARATION 9

Preparation of the 5-octanoylsalicylic acid salt of 2,4-diainopyraidine 3-oxide

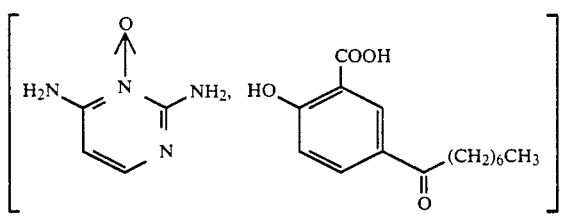

A mixture of 1 g of 2,4-diaminopyrimidine 3-oxide and 1.83 g of 5-octanoylsalicylic ac [sic]is recrystallized from 50 ml of ethanol. A white solid is recovered which is dried to obtain 2.25 g of 2,4-diaminopyrimidine 3-oxide and 5-octanoylsalicylic acid salt.

Yield=79%

Melting point:=177° C.

Elemental analysis:

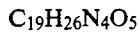

|  | C | H | N | O |
|---|---|---|---|---|
| Calculated | 58.45 | 6.71 | 14.35 | 20.49 |
| Found | 58.50 | 6.67 | 14.27 | 20.63 |

EXAMPLE OF PREPARATION 10

Preparation of 2,4-diamino-5-nitropyrimidine 3-oxide

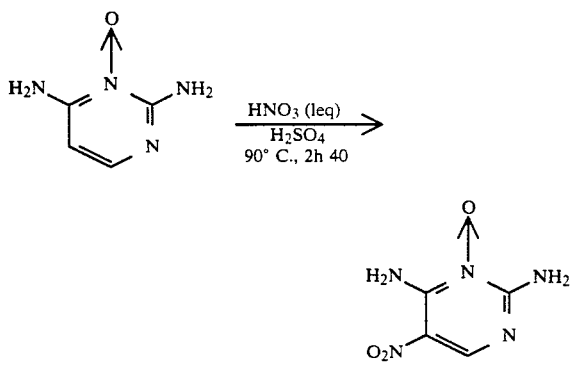

Procedure 2 g of 2,4-diaminopyrimidine 3-oxide are dissolved in 10 ml of concentrated sulfuric acid and then there are added, dropwise and at room temperature, 5 ml of a mixture of 65% HNO$_3$ and concentrated H$_2$SO$_4$ in the following proportions: HNO$_3$:H$_2$SO$_4$=1:4. The reaction is carried out at 90° C. for 2 hours 40 minutes.

The reaction medium is poured onto 250 g of crushed ice and the mixture is neutralized by adding 25 g of KOH pellets, and then with 12 g of NaHCO$_3$ which is introduced in small portions at 0° C. After filtering, the cake is washed with 3×100 ml of water and it is brought to the reflux temperature of an EtOH/H$_2$O mixture (1:1). After filtering, the yellow solid isolated is dried to give 1.4 g of 2,4-diamino-5-nitropyrimidine 3-oxide.

Yield=57%

Melting point higher than 300° C.

Elemental analysis

|  | C | H | N | O |
|---|---|---|---|---|
| Calculated | 28.08 | 2.95 | 40.93 | 28.05 |
| Found | 28.28 | 2.91 | 40.92 | 27.86 |

The $^1$H NMR and mass spectra are consistent with the expected structure,

We claim;

1. Composition intended for topical application, characterized in that it contains, in a physiologically acceptable medium appropriate for a topical application, at least one compound corresponding to the formula (I):

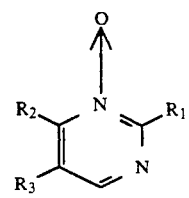

in which:
R$_1$ denotes a methyl or NHR group in which R$_4$ denotes a C$_1$-C$_4$ alkyl group or hydrogen;
R$_2$ denotes hydrogen or a group NHR$_4$ in which R$_4$ has the same meaning as above; R$_2$ may also denote methyl when R$_1$ denotes methyl; when R$_1$ denotes NH$_2$, R$_2$ cannot be hydrogen;
R$_3$ may denote a hydrogen atom or a C$_1$-C$_4$ alkyl group which may optionally carry:
a group OR$_5$ in which R$_5$ denotes a C$_1$-C$_4$ alkyl group,
a benzene nucleus which is optionally substituted by one or more C$_1$-C$_4$ alkoxy groups;
R$_3$ may also denote a halogen atom or a nitro or amino group;
and the physiologically acceptable acid addition salts.

2. Composition according to claim 1, characterized in that the alkyl group denotes methyl or ethyl, the alkoxy group denotes methoxy or ethoxy and the halogen atoms denote chlorine or bromine.

3. Composition according to claim 1, characterized in that the compounds of formula (I) are chosen from the compounds corresponding to the formula (I) in which R$_1$ denotes amino, R$_2$ denotes amino and R$_3$ denotes hydrogen or alternatively chlorine.

4. Composition according to claim 3, characterized in that the physiologically acceptable acid addition salts are chosen from the salts of sulfuric, hydrochloric, phosphoric, acetic, benzoic, salicylic, glycolic, aceturic, succinic, nicotinic, tartaric, maleic, pamoic [sic ], methanesulfonic, picric and lactic acid, and of amino acids.

5. Composition according to claim 1, characterized in that it is provided in the form of a lotion, shampoo, gel, foam, emulsion, vesicular dispersion, soap, spray or aerosol foam.

6. Composition according to claim 1, characterized in that the physiologically acceptable medium is a medium in which the compound of formula (I) is present either in the dissolved state or in the dispersed state.

7. Composition according to claim 1, characterized in that the physiologically acceptable medium consists of water or a mixture of water and a solvent chosen from $C_1$-$C_4$ lower alcohols, alkylene glycols, alkylene glycol and dialkylene glycol alkyl ethers which are present in proportions of between 1 and 80% by weight relative to the total weight of the composition.

8. Composition according to claim 1, characterized in that the medium is thickened by means of thickening agents.

9. Composition according to claim 1, characterized in that it contains one or more agents chosen from esterified oligosaccharides, hexosaccharic acid derivatives, glycosidase inhibitors, glycosaminoglycanase and proteoglycanase inhibitors, tyrosine kinase inhibitors, hyperemics, UV-A- and/or UV-B-screening agents, phosphodiesterase inhibitor, adenine cyclase activators; antioxidants and free radical scavengers, antidandruff agents, moisturizing agents, antiseborrheic agents, steroidal and nonsteroidal anti-inflammatory agents, antiandrogenic agents, hormones, retinoids, antibacterial agents, calcium-antagonising agents, phospholipids, diazoxide, linoleic or linolenic acids, anthralin andsanthracene derivatives, S-alkanoylsalicylic acid and its derivatives, penetration activators, and vitamins or provitamins.

10. Composition according to claim 1, characterized in that the composition additionally contains preservatives, stabilizers, pH-regulating agents, osmotic pressure modifying agents, emulsifiers, UV-A- and UV-B-sunscreens, antioxidants and perfumes.

11. Composition according to claim 1, characterized in that it contains, by way of surface-active agent, surface-active agents chosen from nonionic and amphoteric surface-active agents.

12. Composition according to claim 11, characterized in that the nonionic surface-active agents are chosen from polyhydroxypropyl ethers, oxyethylenated ($C_8$-$C_9$)-alkylphenols containing from 1 to 100 moles of ethylene oxide, alkylpolyglucosides of formula:

$$C_nH_{2n+1}(C_6H_{10}O_5)_xH \tag{III}$$

and in that the amphoteric surface-active agents are chosen from amphocarboxyglycinates and amphocarboxypropionates.

13. Composition according to claim 1, characterized in that the medium consists of a ternary volatile mixture of alkylene glycol alkyl ether, ethyl alcohol and water.

14. Composition according to claim 1, characterized in that the medium is provided in the form of a gel or a thickened medium containing, by way of thickeners, heterobiopolysaccharides, cellulose derivatives, polyhydroxyethyl acrylates or methacrylates or polyacrylic acids crosslinked by means of a polyfunctional agent.

15. Composition according to claim 1, characterized in that it also contains a cationic and/or anionic surface-active agent.

16. Use of the compound corresponding to the formula (I) as defined in claim 1 in the nontherapeutic treatment of hair loss.

17. Process for the cosmetic treatment of hair or the scalp, characterized in that at least one composition as defined in claim 1 is applied to the scalp.

18. Composition according to claim 1, for application in the therapeutic treatment of hair loss.

19. Use of compounds corresponding to the formula (I) as defined in claim 1 for the preparation of a composition intended to be used in the therapeutic treatment of hair loss, in particular of alopecia.

* * * * *